United States Patent [19]

Carrell et al.

[11] Patent Number: 5,679,711
[45] Date of Patent: Oct. 21, 1997

[54] HYDROXYL IONS AS NOVEL THERAPEUTIC AGENTS AND COMPOUNDS THAT MODULATE THESE IONS, COMPOSITIONS EMPLOYING THESE AGENTS, THERAPEUTIC METHODS FOR USING SUCH AGENTS

[75] Inventors: Delton R. Carrell; Edward J. Cragoe, Jr., both of Nacogdoches, Tex.

[73] Assignee: FHJ Scientific, Inc., Houston, Tex.

[21] Appl. No.: 485,926

[22] Filed: Jun. 7, 1995

Related U.S. Application Data

[63] Continuation-in-part of Ser. No. 295,988, Aug. 25, 1994, Pat. No. 5,514,808, which is a continuation-in-part of Ser. No. 134,137, Oct. 8, 1993, Pat. No. 5,585,391.

[51] Int. Cl.$^6$ .................... A61K 31/19; C07C 229/02
[52] U.S. Cl. .................. 514/557; 562/441; 562/442; 562/443; 562/444; 562/451; 562/505; 562/506; 562/507; 562/567; 562/575
[58] Field of Search .................... 562/441, 442, 562/443, 444, 451, 505, 506, 507, 567, 575; 514/357, 557

[56] References Cited

U.S. PATENT DOCUMENTS

| | | | |
|---|---|---|---|
| 3,075,924 | 1/1963 | Rubin | 514/561 |
| 3,151,084 | 9/1964 | Schiltz | 252/542 |
| 3,492,238 | 1/1970 | Wohlberg | 252/87 |
| 3,920,020 | 11/1975 | Kraskin | 128/282 |
| 3,932,607 | 1/1976 | Hesselgren | 424/52 |
| 3,935,862 | 2/1976 | Kraskin | 128/282 |
| 3,965,048 | 6/1976 | Murtaugh | 252/527 |
| 3,975,313 | 8/1976 | Shelmire, Jr. | 252/542 |
| 4,107,331 | 8/1978 | Rosenberg | 424/319 |
| 4,337,269 | 6/1982 | Berke et al. | 424/289 |
| 4,528,370 | 7/1985 | Lai | 514/561 |
| 4,584,121 | 4/1986 | Blaschke et al. | 252/106 |
| 4,767,786 | 8/1988 | Farrish | 514/561 |
| 4,847,083 | 7/1989 | Clark | 424/642 |
| 4,868,213 | 9/1989 | Farrish | 514/561 |
| 4,915,864 | 4/1990 | Kita et al. | 252/117 |
| 5,015,409 | 5/1991 | Read, Jr. et al. | 252/108 |

FOREIGN PATENT DOCUMENTS

| | | | |
|---|---|---|---|
| 0106727 | 4/1984 | European Pat. Off. | |
| 0339531 | 2/1989 | European Pat. Off. | |
| 0629606 | 12/1994 | European Pat. Off. | |
| 0045997 | 4/1981 | Japan | 514/561 |

OTHER PUBLICATIONS

Material Safety Data, Jan. 10, 1990; W.R. Grace & Co.; Organic Chemicals Division, 55 Hayden Ave., Lexington, MA, USA 02173.

Technical Information, Jan. 8, 1976; Hampshire, Organic Chemicals Division, W.R. Grace & Co., 55 Hayden Ave., Lexington, MA 01273.

Giraud–Clenet et al, C.R. Acad. Sci. Paris, Ser. C., vol. 268, No. 1, pp. 117–120, 1969.

Farfan, Synthesis, vol. 10, pp. 927–929, 1987.

Advanced Organic Chemistry, Mar., 3rd Ed., p. 307, 1985.

*Primary Examiner*—Zinna Northington Davis
*Attorney, Agent, or Firm*—Frank J. Uxa

[57] ABSTRACT

The invention concerns the discovery of the surprising and unexpected therapeutic effects of hydroxyl ions. The observed medicinal properties of these ions are both novel and broad in scope. The acute corrosive effects and toxicity of hydroxyl ions on living tissue has previously overwhelmed their therapeutic attributes. Unique hydroxyl ion modulating compounds have been discovered and are within the scope of the invention. When used appropriately as companions with hydroxyl ions, these modulating compounds obviate and attenuate the harmful effects of hydroxyl ions, unmasking and revealing their previously unknown and undemonstratable therapeutic properties. These hydroxyl ion modulating compounds do not significantly interfere with the surprising and unexpected therapeutic benefits of the hydroxyl ions. The novel hydroxyl ion modulating compounds are generally characterized as N,N-disubstituted-aminoalkanoate salts and substituted N,N-substituted-aminoalkanoate salts.

18 Claims, No Drawings

HYDROXYL IONS AS NOVEL THERAPEUTIC AGENTS AND COMPOUNDS THAT MODULATE THESE IONS, COMPOSITIONS EMPLOYING THESE AGENTS, THERAPEUTIC METHODS FOR USING SUCH AGENTS

RELATED APPLICATIONS

This application is a continuation-in-part of application Ser. No. 08/295,988, filed Aug. 25, 1994 now U.S. Pat. No. 5,514,808; which is a continuation-in-part of application Ser. No. 08/134,137, filed Oct. 8, 1993, now U.S. Pat. No. 5,585,391. The disclosure of each of these prior applications is incorporated in its entirety herein by reference.

BACKGROUND OF THE INVENTION

The present invention relates to the discovery of the unique use of hydroxyl ions in a wide variety of therapeutic applications. This medicinal property of hydroxyl ions has not been observed previously due to their severe toxicity and tissue irritating effects. However, when a novel hydroxyl ions modulating compound is used as a companion with hydroxyl ion, the harmful effects are attenuated, unmasking their previously unknown novel therapeutic activity. Thus, the invention also relates to a new class of novel compounds that modulate and attenuate the toxic and harmful effects of hydroxyl ions. The invention includes compositions composed of hydroxyl ions and their companion modulating compounds, therapeutic methods of using such compositions and methods of preparing such compositions and their novel components.

Previous to this invention, compositions that were applied to human or animal tissue or administered in a variety of other ways to achieve a desired therapeutic effect possessed substantially neutral pH values. This is because the irritating and toxic effects of such compositions are directly related to their degree of acidity or alkalinity. In contrast this invention allows compositions with elevated pH values to be used therapeutically.

SUMMARY OF THE INVENTION

The present invention involves the discovery of the novel and wide-ranging therapeutic benefits of hydroxyl ions. A new class of compounds, as well as compositions, therapeutic methods and production processes have been discovered. Severe tissue irritation, toxicity and damage have heretofore been the normal consequence of exposing animal and human tissues to even modest concentrations of hydroxyl ions, for example, sufficient to provide a pH value of above about 8. In total and complete contrast to such detrimental effects of hydroxyl ions, it has unexpectedly and surprisingly been found that hydroxyl ions, when used in combination with one or more of a new class of hydroxyl ion modulating compounds as set forth herein, not only do not exhibit the above-noted detrimental effects but very effective in providing a wide range of advantageous therapeutic effects and other benefits. Such advantageous results are achieved at pH values above about 10, for example, about 12, or even above about 13, for example, about 14. Thus, the hydroxyl ions modulating compounds of this new class of compounds selectively affect or modulate the properties of hydroxyl ion substantially reducing or eliminating the detrimental effects that hydroxyl ions normally have on human and animal tissues, while allowing the unexpected advantageous therapeutic effects and other benefits of hydroxyl ions to be manifest.

Hydroxyl ion, in combination with the present hydroxyl ions modulating compounds, have been found to be highly effective in pharmaceutical and other compositions in providing substantial benefits. For example, the harmful effects of the hydroxyl ions are modulated without substantially interfering with the surprising and unexpected benefits that can be obtained from hydroxyl ion-containing compositions, such as the present compositions, once the harmful effects of the hydroxyl ions have been modulated. The new class of compounds may, in fact, assist the hydroxyl ions in achieving the benefits, for example, the desired therapeutic effects and other beneficial results such as in products used for wound healing and in treating ophthalmic and dental problems, obtained in accordance with the present invention.

The present compositions which include relatively high concentrations of hydroxyl ions unexpectedly provide outstanding and broad-ranging advantageous therapeutic effects and other benefits, while avoiding many of the problems which existed with hydroxyl ions without an accompanying hydroxyl ion modulating agent. The present compositions have been found to provide a wide range of advantageous therapeutic effects, for example, to cure, relieve, manage, heal, treat and/or prevent various conditions, such as ocular conditions, dermal conditions, ear, nose and throat conditions, topical conditions, wound conditions and internal conditions effectively and without undue tissue damage, such as would otherwise be expected from the high concentration of hydroxyl ions present in the composition. The present compositions can be applied to both human and veterinary conditions.

Methods for providing a desired therapeutic effect using the present compositions are included in the scope of the present invention.

Further, processes for producing the present compounds and compositions are included within the scope of the present invention.

In one broad aspect, the present invention is directed to a new class of hydroxyl ion modulating compounds. Such compounds have the formula:

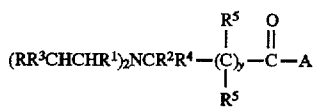

wherein each R is independently selected from the group consisting of H, alkyl, hydroxyalkyl, cycloalkyl, aryl and substituted counterparts thereof; each $R^1$ is independently selected from the group consisting of H, alkyl, hydroxyalkyl and substituted counterparts thereof; $R^2$ is selected from the group consisting of H, alkyl, cycloalkyl, aryl, aralkyl, heterocyclic, heterocyclicalkyl and substituted counterparts thereof; each $R^3$ is independently selected from the group consisting of H, alkyl, hydroxyalkyl, hydroxy, aryl, and substituted counterparts thereof; $R^4$ is selected from the group consisting of H, alkyl having 1 to 4 carbon atoms, lower alkenyl, lower alkynyl and phenyl; y is an integer in the range of zero to 3; each $R^5$ is independently selected from the group consisting of H and methyl; A is selected from the group consisting of $O^-Y^+$, $OCH_2COO^-Y^+$, $OCH(CH_3)COO^-Y^+$, $OC(CH_3)_2COO^-Y^+$, $NHCH_2COO^-Y^+$, $NHCH(CH_3)COO^-Y^+$, $NHC(CH_3)_2COO^-Y^+$, $N(CH_3)CH_2COO^-Y^+$ and $NH(CH_2)_2COO^-Y^+$; and $Y^+$ is selected from the group consisting of $H^+$, $Na^+$, $K^+$, $Li^+$ $(CH_3)_4N^+$ and guanidinium, provided that in the event y is zero or A is $O^-Y^+$, then $R^2$ and/or $R^4$ are other than H, and/or at least one $(RR^3CHCHR^1—)$ includes a hydroxy group. Since each R, $R^1$ and $R^3$ is selected independently of the other R, $R^1$ and $R^3$, respectively each $RR^3CHCHR^1$— group can be the same or different. In one embodiment, y is in the range of 1 to 3.

In one useful embodiment, each R is independently selected from the group consisting of H, alkyl having 1 to 4 carbon atoms, hydroxyalkyl having 1 to 4 carbon atoms, cycloalkyl, phenyl and substituted counterparts thereof; each $R^1$ is independently selected from the group consisting of H, alkyl having 1 to 3 carbon atoms, hydroxyalkyl having 1 to 3 carbon atoms and substituted counterparts thereof; $R^2$ is selected from the group consisting of H, alkyl having 1 to 5 carbon atoms, hydroxyalkyl having 1 to 5 carbon atoms, cycloalkyl having 3 to 6 carbon atoms, aryl, heterocyclic, heterocyclicalkyl and substituted counterparts thereof; each $R^3$ is independently selected from the group consisting of H, alkyl having 1 to 3 carbon atoms, hydroxyalkyl having 1 to 3 carbon atoms, hydroxy, aryl and substituted counterparts thereof; $R^4$ is selected from the group consisting of H, alkyl having 1 to 4 carbon atoms, lower alkenyl, lower alkynyl and phenyl; and y is zero or

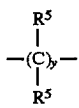

is selected from the group consisting of —$CH_2$—, —$(CH_2)_2$—, —$(CH_2)_3$—, —$CH(CH_3)$— and —$C(CH_3)_2$—.

Preferably, each R in independently selected from the group consisting of H, $CH_3$, $CH_2OH$, and $C_6H_5$; each $R^1$ is independently selected from the group consisting of H, $CH_3$, $CH_2OH$ and $C_2H_5$; $R^2$ is selected from the group consisting of H, $CH_3$, $C_2H_5$, $CH_3CH_2CH_2$—, $HOCH_2$—, cyclopropyl, phenyl, pyridyl, imidazolyl and pyrimidyl; each $R^3$ is independently selected from the group consisting of H, OH, $CH_3$ and $C_2H_5$; $R^4$ is selected from the group consisting of H, vinyl, ethynyl, alkyl having 1 to 4 carbon atoms and phenyl; and y is zero or

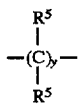

is selected from the group consisting of —$CH_2$—, —$(CH_2)_2$—, $(CH_2)_3$—, —$CH(CH_3)$— and —$C(CH_3)_2$—.

This new class of compounds has surprisingly been found to have the ability to modulate one or more of the detrimental effects of hydroxyl ions, without unduly diminishing the beneficial effect or effects of such hydroxyl ions. In addition, such compounds, or mixtures of such compounds, can be effective in assisting, when used in combination with hydroxyl ions, in achieving certain desired therapeutic effects and other benefits.

It is indeed surprising that this new class of compounds, as set forth herein, has the unexpected utility or ability to effectively modulate one or more detrimental effects of hydroxy ions. For example, the present compounds are different from the compounds disclosed in the above-noted related applications.

In another broad aspect of the present invention, pharmaceutical compositions useful in providing at least one desired therapeutic effect when administered to a human or an animal are provided. Such compositions comprise a therapeutically effective amount of a hydroxyl ion modulating component. The hydroxyl ion modulating component is selected from N,N-disubstituted-aminoalkanoate salts, substituted N,N-disubstituted-aminoalkanoate salts, derivatives thereof and mixtures thereof. The hydroxyl ion modulating component is preferably present in the compositions in a molar concentration greater than the molar concentration of the hydroxyl ion component. The hydroxyl ion modulating component is preferably selected from one or more of the hydroxyl ion modulating compounds described elsewhere herein. In one embodiment, the present compositions are such that the hydroxyl ion modulating component is selected from sodium salts of an acid, potassium salts of an acid, tetramethylammonium salts of an acid and guanidinium salt of an acid; which acid is selected from the group consisting of 2-[N,N-bis-(2-hydroxyethyl)amino]-2-methylpropanoic acid, 2-[N,N-bis-(2-hydroxypropyl)amino]-2-methylpropanoic acid, 2-[N-(2-hydroxyethyl)-N-(2-hydroxypropyl)amino]-2-methylpropanoic acid, 2-[N,N-bis-(2-hydroxyethyl)amino]-2-methylbutanoic acid, the racemate, the D-enantiomer and the L-enantiomer, 2-[N,N-bis-(2-hydroxyethyl)amino]-2-phenylpropanoic acid, 2-[N,N-bis-(2-hydroxyethyl)aminoacetoxy]-2-methylpropanoic acid,

[N,N-bis-(2-hydroxyethyl)aminoacetamido]acetic acid,

N-methyl-N-(N, N-bis-(2-hydroxyethyl)aminoacetamido] acetic acid,

3-[N,N-bis-(2-hydroxyethyl)amino]propanoic acid,

4-[N,N-bis-(2-hydroxyethyl)amino]butanoic acid, 2,2-dimethyl-3-[N,N-bis-(2-hydroxyethyl)amino]propanoic acid, 2-[N,N-bis-(2-hydroxyethyl)amino]-2-(3-pyridyl)propanoic acid, 2-[N,N-bis-(2,3-dihydroxypropyl)amino]-2-methylpropanoic acid, 2-[N,N-bis-(1-hydroxy-2-propyl)amino]-2-methylpropanoic acid, 2-[N,N-bis-(2-hydroxy-2-phenylethyl)amino]-2-methylpropanoic acid, 2-[N,N-bis-(1,3-dihydroxy-2-propyl)amino]-2-methylpropanoic acid, 2-[N,N-bis-(3-hydroxypropyl)amino]-2-methylpropanoic acid and mixtures thereof.

The molar ratio of hydroxyl ion modulating component to hydroxyl ion component is preferably greater than about 1 and less than about 15, more preferably in the range of about 2.5 to about 12. These features further clearly distinguish the present compositions from compositions described previously, for example, in the above-noted related applications.

In one embodiment, the present pharmaceutical compositions are ophthalmically acceptable and are useful in providing a desired therapeutic effect, for example, an ocular analgesic effect, to a mammalian eye when administered thereto.

Ophthalmically acceptable compositions which include a hydroxyl ion component and an effective amount of a hydroxyl ion modulating component are useful in products for treating a variety of ophthalmic problems. The hydroxyl ion component is present in such compositions in an amount which in combination with the hydroxyl ion modulating component is effective in providing one or more benefits to each particular ophthalmic problem.

In another broad aspect of the present invention, methods for providing desired therapeutic effects to a human or an animal are provided. Such methods comprise administering to a human or an animal of the desired therapeutic effect an amount of one of the pharmaceutical compositions described herein. Such amount of pharmaceutical composition is effective in providing the desired therapeutic effect to a human or an animal. Among the desired therapeutic effects that can be obtained using the present pharmaceutical compositions are ocular therapeutic effects, including analgesia of the eye, oral therapeutic effects, ear, nose and throat therapeutic effects, dermal therapeutic effects, topical therapeutic effects, wound therapeutic effects, and internal therapeutic effects. Of course, more than one desired therapeutic effect, even more than one different type of therapeutic effect, can be obtained by a single administration of the present pharmaceutical compositions to the human or animal. In one particularly useful embodiment, the desired therapeutic effect includes at least one of the management of a wound, the healing of a wound and the reduction of pain from a wound. The present compositions possess outstanding and remarkable wound healing properties including, but not limited to, the control of microbial action, edema, erythema and pain, and also act to enhance or improve the quality of scar tissue, for example, relative to scar tissue from an identical wound not treated with such compositions.

Methods for providing a desired therapeutic effect to a mammalian eye are also included. Such methods comprise administering to a mammalian eye an amount of the ophthalmically acceptable pharmaceutical compositions described herein effective in providing the desired therapeutic effect to the mammalian eye. In addition, methods for producing analgesia in the eye are provided using an effective amount of the ophthalmically acceptable compositions described herein at conditions effective in imparting relief of pain in the eye.

Processes for the preparation of compositions comprising an hydroxyl ion modulating component are also within the scope of the present invention. Such hydroxyl ion modulating component is selected from the group of compounds having the formula

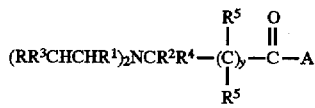

wherein each R is independently selected from the group consisting of H, alkyl, hydroxyalkyl, cycloalkyl, aryl and substituted counterparts thereof; each $R^1$ is independently selected from the group consisting of H, alkyl, hydroxyalkyl and substituted counterparts thereof; $R^2$ is selected from the group consisting of H, alkyl, cycloalkyl, aryl, aralkyl, heterocyclic, heterocyclicalkyl and substituted counterparts thereof; each $R^3$ is independently selected from the group consisting of H, alkyl, hydroxyalkyl, hydroxy, aryl and substituted counterparts thereof; $R^4$ is independently selected from the group consisting of H, alkyl having 1 to 4 carbon atoms, lower alkenyl, lower alkynyl and phenyl; y is an integer in the range of zero to 3; each $R^5$ is independently selected from the group consisting of H and methyl; A is selected from the group consisting of $—O^-Y^+$, $OCH_2COO^-Y^+$, $—OCH(CH_3)COO^-Y^+$, $—OC(CH_3)_2COO^-Y^+$; $—NHCH_2COO^-Y^+$, $NHCH(CH_3)COO^-Y^+$, $—NHC(CH_3)_2COO^-Y^+$; $—N(CH_3)CH_2COO^-Y^+$ and $—NH(CH_2)_2COO^-Y^+$; and $Y^+$ is selected from the group consisting of $Na^+$, $K^+$, $Li^+$, $(CH_3)_4N^+$ and guanidinium, provided that in the event y is zero or A is $O^-Y^+$, then $R^2$ and $R^4$ are other than H.

Such processes comprise contacting a compound having the formula

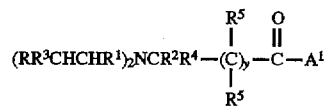

wherein $A^1$ is OH, $OCH_2COOH$, $OCH(CH_3)COOH$, $OC(CH_3)_2COOH$, $NHCH_2COOH$, $NHCH(CH_3)COOH$, $NHC(CH_3)_2COOH$ and $N(CH_3)CH_2COOH$ and $NH(CH_2)_2COOH$ with a molar excess of YOH at effective reaction conditions to form a reaction product including said hydroxyl ion modulating component.

This contacting preferably occurs in the presence of at least about 1.0667 or about 1.07 to about 1.50 molar equivalents of YOH. The reaction product is preferably processed by forming a solution using pyrogen-free water so that the solution contains about 0.1% to about 20% by weight of the product. The product produced by the present processes includes the hydroxyl ion modulating component and is preferably combined with sufficient hydroxyl ion component, for example, the YOH used in the above-noted treatment step, to yield a formulation having a molar ratio of hydroxyl ion modulating component to hydroxyl ion component as described herein with regard to the present compositions, preferably in the range of more than about 1 to about 15 and more preferably about 2.5 to about 12.

DETAILED DESCRIPTION OF THE INVENTION

Hydroxyl ions have been discovered to possess a wide variety of surprising therapeutic effects.

Certain compounds and mixtures of such compounds have unexpectedly been found to have the outstanding and beneficial property of modulating and/or attenuating one or more of the harmful effects of hydroxyl ions, preferably without substantially interfering with the surprising benefits that have been found obtainable from hydroxyl ion component-containing compositions, such as the present compositions, once the harmful effects of the hydroxyl ion component, in particular the hydroxyl ions, have been modulated. In addition, the present compounds and mixtures thereof can assist, when used in combination with hydroxyl ions, in achieving benefits, for example, desired therapeutic effects and other beneficial results.

The present compounds are generally described as N,N-disubstituted-aminoalkanoate salts, substituted N,N-disubstituted-aminoalkanoate salts, derivatives thereof and mixtures thereof. A useful group of compounds are those having the formula:

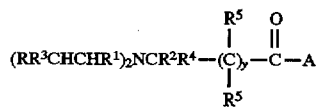

wherein each R is independently selected from the group consisting of H, alkyl, hydroxyalkyl, cycloalkyl, aryl and substituted counterparts thereof; each $R^1$ is independently selected from the group consisting of H, alkyl, hydroxyalkyl and substituted counterparts thereof; $R^2$ is selected from the group consisting of H, alkyl, cycloalkyl, aryl, aralkyl, heterocyclic, heterocyclicalkyl and substituted counterparts thereof; each $R^3$ is independently selected from the group consisting of H, alkyl, hydroxyalkyl, hydroxy, aryl, and substituted counterparts thereof; $R^4$ is selected from the group consisting of H, alkyl having 1 to 4 carbon atoms, lower alkenyl, lower alkynyl and phenyl; y is an integer in the range of zero to 3; each $R^5$ is independently selected from the group consisting of H and methyl; A is selected from the group consisting of $O^-Y^+$, $OCH_2COO^-Y^+$, $OCH(CH_3)COO^-Y^+$, $OC(CH_3)_2COO^-Y^+$, $NHCH_2COO^-Y^+$, $NHCH(CH_3)COO^-Y^+$, $NHC(CH_3)_2COO^-Y^+$, $N(CH_3)CH_2COO^-Y^+$ and $NH(CH_3)_2COO^-Y^+$; and $Y^+$ is selected from the group consisting of $H^+$, $Na^+$, $K^+$, $(CH_3)_4N^+$ and guanidinium, provided that in the event y is zero or A is $O^-Y^+$, then $R^2$ and $R^4$ are other than H, and at least one ($RR^3CHCHR^1$—) includes a hydroxy group.

A preferred group of such compounds are those in which each R is independently selected from the group consisting of H, $CH_3$, $CH_2OH$, and $C_6H_5$; each $R^1$ is independently selected from the group consisting of H, $CH_3$, $CH_2OH$ and $C_2H_5$; $R^2$ is selected from the group consisting of H, $CH_3$, $C_2H_5$, $CH_3CH_2CH_2$—, $HOCH_2$—, cyclopropyl, phenyl, pyridyl, imidazolyl and pyrimidyl; each $R^3$ is independently selected from the group consisting of H, OH, $CH_3$ and $C_2H_5$; $R^4$ is selected from the group consisting of H, vinyl, ethynyl, alkyl having 1 to 4 carbon atoms and phenyl; and y is zero or

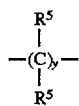

is selected from the group consisting of —$CH_2$—, —$(CH_2)_2$—, —$(CH_2)_3$—, —$CH(CH_3)$— and —$C(CH_3)_2$—.

Preferably at least one R is hydroxyalkyl or at least one $R^3$ is hydroxy or hydroxyalkyl. More preferably, each R is independently selected from hydroxy and hydroxymethyl. In one embodiment, R or $R^1$ is hydroxymethyl and/or each $R^3$ is hydroxy. When $R^2$ is H, $CH_3$ or $CH_2OH$, $R^4$ is H, A is $O^-Y^+$, and y is zero, one or both $RR^3CHCHR^1$— groups are other than $CH_2OHCH_2$— or $CH_3CHOHCH_2$—.

Alkyl is any saturated non-aromatic hydrocarbon radical. Examples of the alkyl group from which certain of the above-noted substituents can be chosen include, but are not limited to, such groups having 1 to about 5 or more carbon atoms, such as methyl, ethyl, propyl, isopropyl, butyl, isobutyl, t-butyl and the like. Examples of the hydroxyalkyl groups from which certain of the above-noted substituents can be chosen include, but are not limited to, such groups having 1 to about 5 or more carbon atoms, such as the alkyl groups noted above substituted with one or more, preferably only one, hydroxyl group.

Hydroxyl group or groups can be located at any point or points on the alkyl chain, preferably other than on the alpha carbon atom, for example, on the beta or gamma carbon atom of the alkyl chain. Examples of cycloalkyl groups from which certain of the above-noted substituents can be chosen include, but are not limited to, such groups having about 3 to about 7 or more carbon atoms, such as cyclopropyl, cyclobutyl, cyclopentyl, cyclohexyl and the like.

Aryl is any hydrocarbon radical having an available bonding site on an aromatic hydrocarbon ring. Examples of the aryl groups from which certain of the above-noted substituents can be chosen include, but are not limited to, such groups having 6 to about 9 or more carbon atoms, such as phenyl, indenyl, condensed aromatic compounds and the like. Examples of the aralkyl groups from which certain of the above-noted substituents can be chosen include, but are not limited to, such groups having 7 to about 12 or more carbon atoms, such as phenylmethyl, phenylethyl, phenylbutyl, phenylhexyl and the like.

Heterocyclic is any radical including a ring having at least one carbon atom and at least one heteroatom (an atom other than a carbon atom), such as N, S, O and the like. Examples of the heterocyclic groups from which certain of the above-noted substituents can be chosen include, but are not limited to, such groups having about 4 to about 8 or more carbon atoms, such as

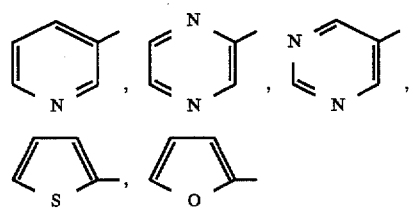

and the like. Examples of the heterocyclicalkyl groups from which certain of the above-noted substituents can be chosen include, but are not limited to, such groups having about 5 to about 10 or more carbon atoms, such as

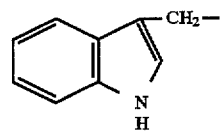

and the like.

The term "substituted counterpart thereof" as it relates to any of the above-noted substituents (other than H) refers to such substituent in which one or more hydrogen atoms are replaced by one or more other species including, but not limited to, monovalent hydrocarbon groups, such as alkyl, alkenyl and alkynyl (such as ethenyl, propenyl, butenyl, ethynyl and the like unsaturatedhydrocarbon groups having 2 to about 6 or more carbon atoms and aryl; heterocyclic groups; halo such as F, Cl, Br and I; $NH_2$; $NO_2$; alkoxy; alkylthio; aryloxy; arylthio; alkanoyl; alkanoyloxy; aroyl; aroyloxy; acetyl; carbamoyl; alkylamino; dialkylamino; arylamino; alkylarylamino; diarylamino; alkanoylamino; alkylsulfinyl; alkylsulfenyl; alkylsulfonyl; alkylsulfonylamido; azido; benzyl; carboxy; cyano; guanyl; guanidino; imino; phosphinyl; silyl; thioxo; uredido or vinylidene or where one or more carbon atoms are replaced by one or more other species including, but not limited to, N, O, or S.

In a particularly useful embodiment, each $R^2$ is independently selected from

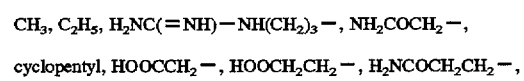

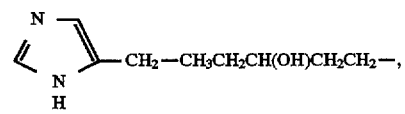

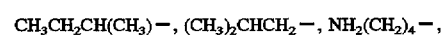

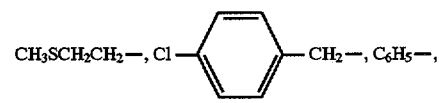

-continued

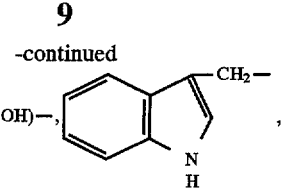

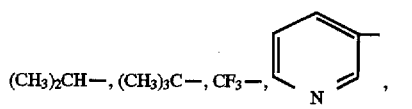

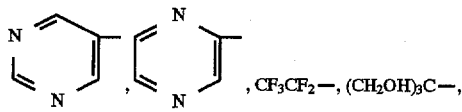

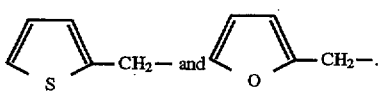

When all of the R, $R^1$, $R^2$, $R^3$ and $R^4$ groups are H and the

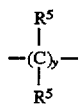

and A moieties are not asymmetric, the above-noted compounds are not chiral. However, when only one R is not H, the compounds are chiral; therefore, the compounds represent a racemate or either of two enantiomers. If any two, three, four, five or all six of the R, $R^1$, $R^2$, $R^3$, $R^4$ and $R^5$ groups are not H and the

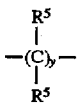

and A moieties are not asymetric, then the above-noted compounds represent any one of two or more diasteriomers or meso forms, and any of the component racemates and enantiomers. This invention includes each of the possible isomers, steroisomers, tautomers and mixtures thereof of the above-noted compounds.

One type of preferred compounds are those derived from natural amino acids, i.e., those in which the

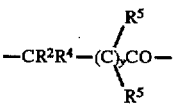

moiety is derived from a natural amino acid. In most instances, these compounds belong to the L-series of amino acids.

Specific examples of hydroxyl ion transmuting compounds include sodium salts, potassium salts, tetramethylammonium salts, tetraethylammonium salts and guanidinium salts and mixtures thereof. Such salts are derived from acids selected from 2-[N,N-bis-(2-hydroxyethyl)amino]-2-methylpropanoic acid, 2-[N,N-bis-(2-hydroxypropyl)amino]-2-methylpropanoic acid, 2-[N-(2-hydroxyethyl)-N-(2-hydroxypropyl)amino]-2-methylpropanoic acid, 2-[N,N-bis-(2-hydroxyethyl)amino]-2-methylbutanoic acid, the racemate, the D-enantiomer and the L-enantiomer, 2-[N,N-bis-(2-hydroxyethyl)amino]-2-phenylpropanoic acid, 2-[N,N-bis-(2-hydroxyethyl)aminoacetoxy]-2-methylpropanoic acid,

[N,N-bis-(2-hydroxyethyl)aminoacetamido]acetic acid,

N-methyl-N-(N,N-bis-(2-hydroxyethyl)aminoacetamido] acetic acid,

3-[N,N-bis-(2-hydroethyl)amino]propanoic acid,

4-[N,N-bis-(2-hydroxyethyl)amino]butanoic acid, 2,2-dimethyl-3-[N,N-bis-(2-hydroxyethyl)amino]propanoic acid, 2-[N,N-bis-(2-hydroxyethyl)amino]-2-(3-pyridyl)propanoic acid, 2-[N,N-bis-(2,3-dihydroxypropyl)amino]-2-methylpropanoic acid, 2-[N,N-bis-(1-hydroxy-2-propyl)amino]-2-methylpropanoic acid, 2-[N,N-bis-(2-hydroxy-2-phenylethyl)amino]-2-methylpropanoic acid, 2-[N,N-bis-(1,3-dihydroxy-2-propyl)amino]-2-methylpropanoic acid, 2-[N,N-bis-(3-hydroxypropyl)amino]-2-methylpropanoic acid and mixtures thereof.

This invention further comprises therapeutic combinations or compositions of the hydroxyl ion modulating component, as described herein, and an hydroxyl ion component. The hydroxyl ion component concentration can be obtained by combining excess base (YOH) with the substituted or unsubstituted N,N-aminoalkanoate salt or salts. A wide range of hydroxyl ion component concentrations are uniquely therapeutically effective. In order to obtain a more effective hydroxyl ion effect, the molar concentration of the hydroxyl ion modulating component in the present compositions is preferably greater than the molar concentration of the hydroxyl ion component. In one embodiment, the molar ratio of the hydroxyl ion modulating component (or HIMC) to the hydroxyl ion component (or HIC) is greater than about 1 and less than about 15. More preferably, the molar ratio of HIMC to HIC in the present compositions is in the range of about 2 or about 2.5 to about 10 or about 12. When used in aqueous solutions, the preferred molar concentration range for the hydroxyl ion modulating component is in the range of about 0.01 to about 2.2.

The innovative compositions of this invention may be prepared as solutions, powders, mouth washes, ointments, creams, gels and other convenient pharmaceutical forms. Effective amounts of appropriate, for example, conventional and well known, ingredients, such as carriers and the like, may be included in order to provide the desired form of the present compositions.

Although the present compositions may be stored for use and/or administered as a solid, e.g., powder, or other form, in use these compositions are combined with a medium effective to ionize the hydroxyl ion component to form hydroxyl ions. In many instances, this ionizing medium is aqueous-based. For example, if the composition is administered as a powder to the skin of a human or animal, moisture on the skin (for example perspiration or even blood on the skin) can act as the ionizing medium to form an effective amount of hydroxyl ions which are effectively modulated by the hydroxyl ion modulating component, which preferably is also ionized by the ionizing medium. In a particularly useful embodiment, the present compositions include an effective amount, for example, at least about 20% or at least about 95% by weight, of an ionizing medium, more preferably an aqueous-based ionizing medium, such as pyrogen-free water. Including the ionizing medium in the present compositions effectively controls the effective concentration of hydroxyl ions in such compositions and, in certain instances, increases the convenience of administering the compositions to human or animals.

The compositions of the present invention preferably contain about 0.05% to about 30% or more by weight of active ingredients, for example, HIMC and HIC. The compositions may also be concentrated, for example, lyphilization or vacuum volatilization of a portion of the solvent, as desired for other purposes.

One or more other ingredients may be added to the compositions, as desired, including, but not limited to, dyes, pigments, perfumes, etc., for example, up to a total of about 10% by weight. Also, for application to human or animal tissue, the compositions may contain components normally present in preparations for this purpose, such as emulsifiers, fatty substances, plant extracts, preservatives, tonicity adjusters and solvents in the customary, effective amounts. The compositions of the present invention may contain any constituent which is not unduly irritating to human or animal tissue either alone or in combination with the active ingredients, and does not significantly affect the pH of the composition. The present compositions are preferably free of cationic surface active agents.

The present invention includes methods for providing one or more desired therapeutic effects to a human or an animal. Such methods comprise administering to a human or an animal in need of the desired therapeutic effect or effects an amount of the present pharmaceutical compositions effective in providing the desired therapeutic effect or effects to a human or animal. Such desired therapeutic effects can result or be embodied in or lead to the mitigation, for example, the curing, relieving, managing, healing, treating and/or preventing, of various conditions. Among the desired therapeutic effects that can be obtained using the present compositions are ocular therapeutic effects, oral therapeutic effects, ear, nose and throat therapeutic effects, dermal therapeutic effects, topical therapeutic effects, wound therapeutic effects (that is therapeutic effects to wounds, in particular wound healing effects) and internal therapeutic effects.

Among the ocular therapeutic effects that can be obtaining using the present compositions are: ocular wound healing effects, ocular disinfecting effects, ocular analgesic effects and ocular antiseptic effects. The present ocular therapeutic effects are preferably obtained by administering to a mammalian eye or eyes an amount of the present therapeutic composition effective in providing the desired therapeutic effect to the mammalian eye or eyes.

When used to provide ocular therapeutic effects or to care for contact lenses, the present compositions preferably are ophthalmically acceptable. The term "ophthalmically acceptable" refers to the property of a composition whereby no significant long term detrimental effect results if an effective amount of the composition is administered to the eye or eyes of a human or animal, in particular to the eye or eyes of a mammal. One would expect that the present compositions with relatively large hydroxyl ion concentrations would cause irritation, or even damage, to the mammalian eye, which is one of the most sensitive body organs. Thus, it is indeed surprising and unexpected that the present hydroxyl ion-containing compositions are effective in providing ocular therapeutic effects and in caring for contact lenses, and are, at the same time, ophthalmically acceptable.

Among the oral therapeutic effects that can be obtained using the present compositions include the treatment and/or management of gingivitis, plaque removal and prevention, healing of oral wounds, for example, from dental and surgical procedures, treatment and/or management of cold and other mouth sores. The present compositions can also be used to deodorize the mouth, and to provide oral antiseptic effects and oral analgesic effects. Among the ear, nose and throat therapeutic effects that can be provided using the present compositions are the reduction and elimination of ear infections and ear pain; the treatment and/or management of swimmer's ear; as an ear, nose and throat antiseptic; as a nasal spray to provide decongestion; and as a treatment and/or management agent for sore throat.

Among the dermal therapeutic effects that can be obtained using the present compositions are healing of dermal wounds, meaning to include, but not limited to, burn healing, and the treatment and/or management of ache, sunburn, diaper rash, jock itch and boils. Also, the present compositions can be used to treat contact dermatitis, for example, insect bites/stings, poison ivy/oak and the like; hemorrhoids; vaginal infections, for example, yeast infections; fungal and bacterial infections, for example, athlete's foot, ringworm and the like; cuts and abrasions, for example, to provide antimicrobial, antiedema and antierythemia advantages, as well as relief of pain, improvement of the quality of scar tissue and the like; psoriasis; inflammation; decubitus ulcers; pain; eczema; dermatitis; scabies; shingles; hot spots, for example, on animals such as dogs and the like; and mange in animals. The present compositions can also be used as deodorants.

Among the internal therapeutic effects which can be obtained using the present compositions are wound healing, including, but not limited to, post-surgical wound healing; wound cleaning and disinfecting; analgesic effects; antimicrobial effects; pain reduction and the like.

One primary therapeutic use for the compositions of this invention is for wound healing. The advantage of this therapy is that a contribution is made to more than one, even many, facets of wound healing. Such facets include, but are not limited to, one or more of the following: antimicrobial effects; reduction of local edema and erythema; abatement of pain; increase in the rate of healing; and improvement in scar tissue quality. The wounds can involve one or more of a variety of tissue lesions including cuts, abrasions, surgical lesions, burns, sunburn, etc. The wounds can be caused by accidents or by disease processes such as ache, bed sores, boils, skin and mouth ulcers, gingivitis, etc. The application of the described therapy can be to human or veterinary medical problems.

The therapy can be applied to the skin, mouth, eye, ear or vagina. It can be used as a treatment of an existing medical problem or used prophylactically to prevent lesions, wounds or their sequelae. Examples of the prophylactic use of the compositions of this invention include a solution for the treatment of contact lenses and prevention of dental plaque to avert dental cavities and gingivitis. Skin treatment prior to surgery is also included.

The present hydroxyl ion modulating substituted and unsubstituted aminoalkanoate salts can be prepared by a number of methods. One convenient method comprises the interaction of an appropriate aminoalkanoic acid shown below with an appropriate base (YOH) under conditions effective in neutralizing the acid and forming the corresponding salt.

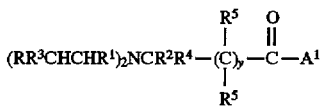

Where $A^1$ is OH, —OCH$_2$COOH, —OCH(CH$_3$)COOH, —OC(CH$_3$)$_2$COOH, —NHCH$_2$COOH, —NHCH (CH$_3$) COOH, —NHC(CH$_3$)$_2$COOH, —N(CH$_3$)CH$_2$COOH, and —NH(CH$_2$)$_2$COOH.

This method is especially useful since, when various combinations or compositions including the present hydroxyl ion modulating aminoalkanoic salts and hydroxyl ion components are desired, excess YOH can be included.

The synthesis of compounds of the type represented by the formula

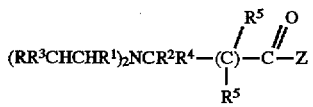 (I)

can be carried out by a variety of synthetic schemes of which the following is an example.

 (II)

is contacted with a second compound having the following formula

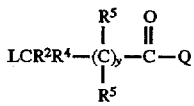 (III)

at effective reaction conditions to produce a third compound having the following formula

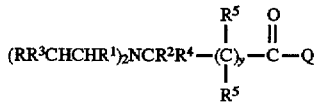 (IV)

which is subjected to pyrolysis conditions to produce

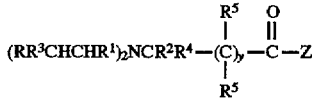 (I)

The contacting, at reaction conditions, of an amine of Formula II with an omega haloalkanoic acid ester of Formula III yields an ester of Formula IV. Pyrolysis of this ester yields the corresponding hydroxyl ion modulating compound (of Formula I) of the present invention. In this series of reactions, R, R$^1$, R$^2$, R$^3$, R$^4$, R$^5$, y, and Z are as described previously, and Q is OR$^6$, —OCH$_2$COOR$^6$, —OCH(CH$_3$)COOR$^6$, —OC(CH$_3$)$_2$COOR$^6$, —NHCH$_3$COOR$^6$, —NHCH(CH$_3$)COOR$^6$, —NHC(CH$_3$)$_2$COOR$^6$, —N(CH$_3$)CH$_2$COOR$^6$, or —NH(CH$_2$)$_3$COOR$^6$, L is a halo group, such as chloro, bromo or iodo, and R$^6$ is a tertiary alkyl group, such as t-butyl, 1,1-dimethylpropyl and the like.

The reaction of compounds of Formula II with those of Formula III can be conducted neat or with solvents, such as an alkanol, for example, ethanol, 2-propanol or 1-propanol, acetonitrile, dimethylformamide and the like. The reaction mixture is conveniently stirred and heated, for example, to temperatures in the range of about 40° C. to the boiling point of the solvent, for a period in the range of about 10 minutes to about 12 hours.

Pyrolysis of a compound of Formula IV can be conducted under catalytic conditions, for example, acidic conditions. It is conveniently conducted in a non-aqueous solvent, such as methanol, ethanol, 1-propanol or 2-propanol, acetonitrile, etc. The solution is conveniently stirred and heated to a temperature in the range of about 40° C. to the boiling point of the solvent for a period in the range of about 30 minutes to about 8 hours. The product may precipitate from the solution and be isolated by filtration or by chromatography, or the reaction mixture may be evaporated in vacuo and the hydroxyl ion modulating compound extracted using an organic solvent. The hydroxyl ion modulating compound can be isolated from a solvent by evaporation in vacuo.

One useful method of producing compounds of Formula IV, and ultimately compounds of Formula I, is illustrated as follows:

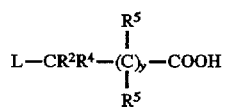 (V)

is contacted with 1,1-carbonyldiimidazole at effective reaction conditions to yield

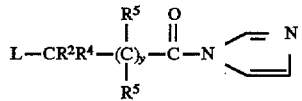 (VI)

which is contacted with HQ at effective reaction conditions to yield

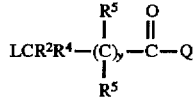 (III)

which can be processed, as described above, to yield a compound of Formula I.

Reactions of compounds of Formula V with 1,1'-carbonyldiimidazole in a solvent, such as tetrahydrofuran, 1,4-dioxane, acetonitrile and the like, produce compounds of Formula VI. The mixture is stirred at temperatures in the range of about 25° C. to the boiling point of the solvent for a period in the range of about 3 to about 48 hours. Reaction of compounds of Formula VI with compounds of Formula HQ by heating, for example, to a temperature in the range of about 40° C. to about 85° C. for a period in the range of about 3 hours to about 12 hours, gives compounds of Formula III which upon reaction with compounds of Formula II produces compounds of Formula IV as described previously. Pyrolysis of compounds of Formula IV produces compounds of Formula I, as described previously.

The present invention is illustrated by the following non-limiting examples wherein all parts and percentages are by weight unless otherwise defined.

Since most of the uses of the compositions of this invention are for application topically to a tissue, they can be applied as powders, ointments, or solutions. The solutions can be conveniently applied as sprays and the solids as aerosols. The concentration of the active ingredient may be in the range of about 0.1% to about 20% depending on the specific preparations and the number of daily applications which may be from once a day or less frequently to hourly or more frequently.

The therapeutic activities described were established by state-of-the-art assays. Some examples are as follows using various dilutions of aqueous solutions of 47.4% by weight of pure sodium [N,N-bis-(2-hydroxyethyl)amino]-2-methylpropanoate+1.5% by weight sodium hydroxide (total solids=48.9%). For convenience this solution is designated as Solution A.

EXAMPLE A: Wound Healing Models

1. Incisional model

Two parallel 6 cm incisions are made through the panniculus of rats and a skin separation of at least 1 cm occurred. 200 microliters of Solution A is instilled in the right wound and 200 microliters in the left wound. This procedure is repeated (with different rats) using a 1:5 dilution and a 1:20 dilution of Solution A with pyrogen-free distilled water. The wound is closed with 6 interrupted 4-0 nylon sutures.

At 7 and 14 days, the animals are sacrificed and 8 mm strips cut from each wound (3 strips per wound, 6 strips per rat). These strips are then disrupted using an Instron 4201 tensiometer and the results expressed as breaking strength in kilograms.

After 14 days, the breaking strength of Solution A, the 1:5 dilution of Solution A, and the 1:20 dilution of Solution A show an increasingly greater breaking strength of the wounds as compared with the control(saline).

2. Chronic model

Briefly, a chronic, granulating wound is created in a rat by excising a full thickness dorsal scald which has be inoculated with E. Coli 5 days after injury. The granulating wound is then treated once with Solution A and, using different rats, with various dilutions (with pyrogen-free distilled water) thereof. Contraction is assessed by serial area measurement of the wound. All areas are expressed as a percentage of the original area and plotted against time. At 7 days a biopsy for quantitative bacteriology is taken to gauge the presence of ongoing infection. At sacrifice the healed wounds are disrupted using the tensiometer as previously described.

After 18 days the percent of the wound that is open for Solution A, a 1:5 dilution of Solution A, and a 1:20 dilution of Solution A show increasingly greater percent of the wound to be closed as compared to saline controls. Longer periods of observation reveal similar differences.

The antibacterial activities of Solution A and 1:5, 1:10., 1:20 and 1:40 dilutions of Solution A (with pyrogen-free distilled water) are evaluated versus E. Coli ($8 \times 10^7$ organisms), Ps. aeruginosa ($6 \times 10^6$ organisms), S. aureus ($4 \times 10^5$ organisms), Strep. pneumoniae ($4 \times 10^6$ organisms), S. epidermidis ($4 \times 10^6$ organisms) and Strep faecalis ($4 \times 10^6$ organisms). Each of these organisms is added to sterile tubes containing 3 ml of the test solution. At times 0, 15, 30, and 60 minutes after addition of the organisms, the solutions are plated (E. Coli and Ps. aeruginosa on McConkey, all others on blood agar). Colony counts are taken after 24 hours of incubation at 37° C.

The effectiveness of the solutions increases with time. By 60 minutes, solution A and each of its four dilutions are completely effective in killing E. Coli and Pa. aeruginosa whereas only the three higher concentrations completely kill S. aureus, Strep. pneumoniae, S. epidermidis and Strep. faecalis.

The effect of Solution A and a 1:20, 1:40, 1:60, 1:80, 1:100 and 1:1000 dilutions of Solution A (with pyrogen-free distilled water) on tissue cultured Vero cells are examined. Vero cells are chosen for the propagation and quantitation of herpes simplex viruses and are transformed African green monkey kidney fibroblasts. The medium used in the Vero cell cultures is Earle's minimal essential medium with supplements. Only a very slight detrimental effect on the tissue culture growth is seen with Solution A. However, no detrimental effect is seen with any of the dilutions.

EXAMPLE 1

Preparation of 2-[N,N-bis-(2-hydroxyethyl)amino]-2-methylpropanoic acid.

Methyl 2-bromo-2-methylpropanoate (181.04 grams, 1 mole) is dissolved in 1-propanol (500 ml.) and bis-(2-hydroxyethyl)amine (105.14 grams, 2 moles) and triethylamine (111.1 grams, 1.1 moles are added and the mixture stirred and heated at reflux for 3 hours. The mixture is treated with 10 normal sodium hydroxide (110 ml., 1.1 moles) and the solvents are removed by distillation in vacuo. The residue is filtered and the solid washed with 1-propanol. The combined filtrates are dissolved in ethanol (400 ml) and 10 normal sodium hydroxide (130 ml, 1.3 moles) is added. The mixture is stirred and heated at reflux for 3 hours. The mixture is acidified with 12 normal hydrochloric acid (108 ml., 1.3 moles). Upon cooling, 2-[N,N-bis-(2-hydroxyethyl)-amino]-2-methylpropanoic acid separates and is collected by filtration, and is washed with a 50% aqueous ethanol and dried.

EXAMPLE 2

Preparation of sodium 2-[N,N-bis-(2-hydroxyethyl)-amino]- 2-methylpropanoate.

2-[N,N-bis-(2-hydroxyethyl)amino]-2-methylpropanoic acid (423.46 grams, 2.21 moles) (this material is about 99% pure; it contains 1% $H_2O$) is added with stirring to a cooled solution of pure sodium hydroxide (88.57 grams, 2.21 moles) in pyrogen-free distilled water (400 ml.). The mixture is stirred until solution is effected. After reaching room temperature, the solution is stirred while enough pyrogen-free distilled water is added to make the total volume 1,000 ml. The solution is sterilized by filtration. This solution contains 47.4% by weight of, or is 2.21 molar in, sodium 2-[N,N-bis-(2-hydroxyethyl)-amino]-2-methylpropanoate.

EXAMPLE 3

Preparation of a combination of sodium 2-[N,N-bis-(2-hydroxyethyl)amino-2-methylpropanoate and sodium hydroxide.

2-[N,N-Bis-(2-hydroxyethyl)amino]-2-methylpropanoic acid (474.39 grams, 2.21 moles) is added with stirring to a cooled solution of pure sodium hydroxide (103.57 grams, 2.59 moles) in pyrogen-free distilled water. The mixture is stirred until solution is effected. After reaching room temperature, the solution is stirred while enough pyrogen-free distilled water is added to make a total volume of 1,000 ml. The solution is sterilized by filtration. This solution contains 47.4% by weight, or is 2.21 molar in, sodium 2-(N,N-bis-(2-hydroxyethyl)-amino]-2-methylpropanoate and contains 1.5% by weight, or is 0.375 molar in, sodium hydroxide. Thus, the mixture contains 48.9% of solute. The molar ratio of sodium 2-[N,N-bis-(2-hydroxyethyl)amino]-2-methylpropanoate to excess hydroxyl ions is 5.9:1. This solution serves as a "stock" solution from which less concentrated solutions can be prepared by diluting 1:5, 1:10, 1:20, 1:50, 1:100, etc. with pyrogen-free sterile distilled water. By using relatively more or less sodium hydroxide as described in Example 3, other combinations are made. One particularly useful molar range of sodium 2-[N,N-bis-(2- hydroxyethyl)amino]-2-methylpropanoate to excess hydroxyl ions is in the range of about 15:1 to about 1:1, and more preferably about 12:1 to about 2.5:1.

EXAMPLE 4

Preparation of other salts of 2-[N,N-bis-(2-hydroxyethyl) amino]-2-methylpropanoic acid.

By carrying out a reaction as described in Example 2 except that the sodium hydroxide is replaced by an equimolar amount of:

a. lithium hydroxide
b. potassium hydroxide
c. tetramethylammonium hydroxide
d. guanidine, there is obtained, respectively, the a. lithium, b. potassium, c. tetramethylammonium, and d. guanidinium salt of 2-[N, N-bis-(2-hydroxyethyl)-amino]-2-methylpropanoic acid.

EXAMPLE 5

Preparation of combinations of other salts of 2-[N,N-bis-(2-hydroxethyl)amino]-2-methylpropanoate and excess base.

By carrying out a reaction as described in Example 3 except that the sodium hydroxide is replaced by an equimolar amount of the bases listed in Example 4 to give combinations of a. lithium 2-[N,N-bis-(2-hydroxyethyl)amino]-2-methylpropanoate and lithium hydroxide,
b. potassium 2-[N,N-bis-(2-hydroxyethyl)amino]-2-methylpropanoate and potassium hydroxide,
c. tetramethylammonium 2-[N,N-bis-(2-hydroxyethyl) amino]-2-methyl-propanoate and tetramethylammonium hydroxide, and
d. quanidinium 2-[N,N-bis-(2-hydroxyethyl)amino]-2-methylpropanoate and guanidine.

EXAMPLE 6

Preparation of salts of 2-[N,N-bis-(2-hydroxyalkyl) amino]-2-methylpropanoic acid.

The procedure as described in Example 1 is repeated eight (8) times except that the bis-(2-hydroxyethyl)amine is replaced by an equimolar amount of one of the following:

1. bis -(2-hydroxypropyl)amine,
2. bis-(2,3-dihydroxypropyl)amine,
3. bis -(1-hydroxy-2-propyl)amine,
4. bis -(2-hydroxy-2-phenylethyl)amine,
5. bis -(1,3-dihydroxy-2-propyl)amine,
6. bis -(3-hydroxypropyl)amine,
7. N-(2-hydroxyethyl)-2-hydroxypropylamine, and
8. N-(2-hydroxyethyl)-3-hydroxypropylamine.

The following products are obtained, respectively:

1a. 2-[N,N-bis-(2-hydroxypropyl)amino]-2-methylpropanoic acid,
2a. 2-[N,N-bis-(2,3-dihydroxypropyl)amino]-2-methylpropanoic acid,
3a. 2-[N,N-bis-(1-hydroxy-2-propyl]amino]-2-methylpropanoic acid,
4a. 2-[N,N-bis-(2-hydroxy-2-phenylethyl)amino]-2-methylpropanoic acid,
5a. 2-N,N-bis-(1,3-dihydroxy-2-propyl)amino]-2-methylpropanoic acid,
6a. 2-N,N-bis-(3-hydroxypropyl)amino]-2-methylpropanoic acid,
7a. 2-[N-(2-hydroxyethyl)-N-(2-hydroxypropyl)amino]-2-methylpropanoic acid and 8a. 2-[N-(2-hydroxyethyl)-N-(3-hydroxypropyl)amino]-1-methylpropanoic acid.

The procedure described in Example 2 is repeated eight (8) times except that each time the procedure is repeated the 2-[N,N-bis-(2-hydroxyethyl)amino]-2-methylpropanoic acid is replaced by one of the eight (8) aminoacetic acids described above. The following products are obtained, respectively:

1b. sodium 2-[N,N-bis-(2-hydroxypropyl)amino]-2-methylpropanoate,
2b. sodium 2-[N,N-bis-(2,3-dihydroxypropyl)amino]-2-methylpropanoate,
3b. sodium 2-[N,N-bis-(1-hydroxy-2-propyl)amino]-2-methylpropanoate,
4b. sodium 2-[N,N-bis-(2-hydroxy-2-phenylethyl)amino]-2-methylpropanoate,
5b. sodium 2-[N,N-bis-(1,3-dihydroxy-2-propyl)amino]-2-methylpropanoate,
6b. sodium 2-[N,N-bis-(3-hydroxypropyl)amino]-2-methylpropanoate,
7b. sodium [N-(2-hydroxyethyl)-N-(2-hydroxypropyl) amino]-2-methyl -propanoate, and
8b. sodium 2-[N,-(2-hydroxyethyl)-N-(3-hydroxypropyl)amino]-2-methylpropanoate.

The procedure described in Example 3 is repeated eight (8) times except that each time the procedure is repeated the 2-[N,N-bis-(2-hydroxyethyl)amino]-2-methylpropanoic acid is replaced by an equimolar amount of one of the eight (8) aminoacetic acids described above. The following products are obtained, respectively:

1c. sodium 2-[N,N-bis-(2-hydroxypropyl)amino]-2-methylpropanoate and sodium hydroxide,
2.c sodium 2-[N,N-bis-(2,3-dihydroxypropyl)amino]-2-methylpropanoate and sodium hydroxide,
3c. sodium 2-[N,N-hydroxy-2-propyl)amino]-2-methylpropanoate and sodium hydroxide,
4c. sodium 2-[N,N-bis-(2-hydroxy-2-phenylethyl)amino]-2-methylpropanoate and sodium hydroxide
5c. sodium 2-[N,N-bis-(1,3-dihydroxy-2-propyl)amino]-2-methylpropanoate and sodium hydroxide,
6c. sodium 2-[N,N-bis-(3-hydroxypropyl)amino]-1-methylpropanoate and sodium hydroxide,
7c. sodium 2-[N-(2-hydroxyethyl)-N-(2-hydroxypropyl) amino]-2-methyl-propanoate and sodium hydroxide, and
8c. sodium 2-[N,-(2-hydroxyethyl)-N-(3-hydroxy-propyl) amino]-2-methylpropanoate and sodium hydroxide.

The procedure described in Example 4 is repeated eight (8) times except that each time the procedure is repeated the 2-[N,N-bis-(2-hydroxyethyl)amino]-2-methylpropanoic acid is replaced by one of the eight (8) aminoacetic acids described above. The following products are obtained, respectively: the (1) lithium, (2) potassium, (3) tetramethylammonium, and (4) guanidinium salts of each one of these aminoalkanoic acids.

The procedure described in Example 5 is repeated eight (8) times except that each time the procedure is repeated the 2-[N,N-bis-(2-hydroxyethyl)amino]-2-methylpropanoic acid is replaced by an equimolar amount of one of the eight (8) aminoalkanoic acids described above. Combinations of one of the four (4) salts of each of the eight (8) aminoalkanoic acids plus the base used to form the salt are obtained.

EXAMPLE 7

Preparation of salts of N,N-bis-(2-hydroxyethyl)aminoacetate substituted on the 2-carbon atom of the acetate moiety.

By following the procedure described in Example 1, except that the methyl 2-bromo-2-methylpropanoate is replaced by an equimolar amount of:

a. methyl 2-bromo-2-methylbutanoate,
b. methyl 2-bromo-2-phenylpropanoate,
c. methyl 3-iodopropanoate,
d. methyl 2,2-dimethyl-3-iodopropanoate,
e. methyl 4-iodobutanoate,
f. methyl 2-bromo-2-(3-pyridyl)propanoate,
g. the L-enantiomer of methyl 2-bromo-2-methylbutanoate and
h. the D-enantiomer of methyl 2-bromo-2-methylbutanoate.

there is obtained, respectively:

a-1. 2-[N,N-bis-(2-hydroxyethyl)amino]-2-methylbutanoic acid,
b-1. 2-[N,N-bis-(2-hydroxyethyl)amino]-2-phenylpropanoic acid,
c-1. 3-[N,N-bis-(2-hydroxyethyl)amino]propanoic acid,
d-1. 3-[N,N-bis-(2-hydroxyethyl)amino]-2,2-dimethylpropanoic acid,
e-1. 4-[N,N-bis-(2-hydroxyethyl)amino]butanoic acid,
f-1. 2-[N,N-bis-(2-hydroxyethyl)amino]-2-(3-pyridyl)propanoic acid,
g-1. the L-enantiomer of 2-[N,N-bis-(2-hydroxyethyl)amino]-2-methylbutanoic acid and
h-1. the D-enantiomer of 2-[N,N-bis-(2-hydroxyethyl)amino]-2-methylbutanoic acid.

By following the procedure described in Example 2 except that the 2-[N,N-bis-(2-hydroxyethyl)amino-2-methylpropanoic acid is replaced by the eight (8) alkanoic acids noted above, there is obtained, respectively, a-2. sodium 2-[N,N-bis-(2-hydroxyethyl)amino]-2-methylbutanoate,
b-2. sodium 2-[N,N-bis-(2-hydroxyethyl)amino]-2-phenylpropanoate,
c-2. sodium 3-[N,N-bis-(2-hydroxyethyl)amino]-propanoate,
d-2. sodium 3-[N,N-bis-(2-hydroxyethyl)amino]-2,2-dimethylpropanoate,
e-2. sodium 4-[N,N-bis-(2-hydroxyethyl)amino]butanoate,
f-2. sodium 2-[N,N-bis-(2-hydroxyethyl)amino]-2-(3-pyridyl) propanoate,
g-2. the L-enantiomer of sodium 2-[N,N-bis-(2-hydroxyethyl)amino]-2-methylbutanoate and
h-2. the D-enantiomer of sodium 2-[N,N-bis-(2-hydroxyethyl)amino]-2-methylbutanoate.

By following the procedure described in Example 3, except that the 2-[N,N-bis -(2-hydroxyethyl)amino -2-methylpropanoic acid is replaced by an equimolar amount of the eight (8) alkanoic acids noted above, there is obtained, respectively, a-3. sodium 2-[N,N-bis-(2-hydroxyethyl)amino]-2-methylpropanoate and sodium hydroxide,
b-3. sodium 2-[N,N-bis-(2-hydroxyethyl)amino]-2-phenylpropanoate and sodium hydroxide,
c-3. sodium 3-[N,N-bis-(2-hydroxyethyl)amino]-propanoate and sodium hydroxide,
d-3. sodium 3-[N,N-bis-(2-hydroxyethyl)amino]-2,2-dimethylpropanoate and sodium hydroxide,
e-3. sodium 4-[N,N-bis-(2-hydroxyethyl)amino]-butanoate and sodium hydroxide,
f-3. sodium 2-[N,N-bis-(2-hydroxyethyl)amino]-2-(3-pyridyl)propanoate and sodium hydroxide,
g-3. the L-enantiomer of sodium 2-[N,N-bis-(2-hydroxyethyl)amino]-2-methylbutanoate and sodium hydroxide and
h-3. the D-enantiomer of sodium 2-[N,N-bis-(2-hydroxyethyl)amino]-2-methylbutanoate and sodium hydroxide.

By following the procedure described in Example 4, except that the 2-[N,N-bis-(2-hydroxyethyl)amino]-2-methylpropanoic acid is replaced by an equimolar amount of the eight (8) substituted alkanoic acids noted above, there is obtained, respectively, the (1) lithium, (2) potassium, (3) tetramethylammonium and (4) guanidinium salts of each of these eight (8) alkanoic acids.

By following the procedure described in Example 5, except that the 2-[N,N-bis-(2-hydroxyethyl)amino]-2-methylpropanoic acid is replaced by an equimolar amount of the eight (8) acetic acids noted above, there is obtained, respectively, the (1) lithium, (2) potassium, (3) tetramethylammonium and (4) guanidinium salts of each of these eight (8) alkanoic acids, each with a molar ratio of substituted acetate salt to excess base in the range of 15:1 to 1:1 by using the same base that was used to prepare the salt.

EXAMPLE 8A

Preparation of salts of [N,N-bis-(2-hydroxyethyl)amino]acetamido]acetic acid with and without excess base.

2-[N,N-Bis-(2-hydroxyethyl)amino]-2-methylpropanoic acid (Example 1) (19.12 grams, 0.1 mole) and 1,1-carbonyldiimidazole (19.45 grams, 0.12 mole) in dry tetrahydrofuran (1000 ml.) is stirred in an atmosphere of nitrogen at ambient temperature for 30 minutes. Glycine methyl ester hydrochloride (14.07 grams, 0.12 mole) and triethylamine (12.1 grams, 0.12 mole) is added and the mixture stirred at ambient temperature for 16 hours. The solvent is removed by distillation in vacuo and the residue dissolved in diethyl ether (750 ml.) washed three times with water (100 ml. portions) and dried over anhydrous magnesium sulfate. The solvent is removed by evaporation in vacuo and the residue treated with ethanol (250 ml.) and 0.2 normal sodium hydroxide (750 ml.). The mixture is stirred and refluxed for 25 minutes whereby a clear solution formed. The mixture is evaporated in vacuo to a volume of 150 ml., cooled in ice and acidified with hydrochloric acid.

The precipitate that separated is removed by filtration, treated with water containing 0.12 mole of sodium bicarbonate, to effect dissolution, filtered and the filtrate acidified with hydrochloric acid. The precipitate that formed is removed by filtration, washed with a little water and dried. The yield of the product is 20.4 grams. This material is chromatographed over silica gel (1500 grams) using a 4 cm by 40 cm column and eluted with methylene chloride/tetrafuran/acetic acid 20/10/2 (by volume). The appropriate fractions are taken and the solvents removed by distillation in vacuo. The residue is treated with water containing 0.12 moles of sodium bicarbonate to effect dissolution, filtered and the filtrate acidified with hydrochloric acid. The precipitate that formed is removed by filtration, washed with water and dried. The yield of [N,N-(2-hydroxyethyl)aminoacetamido]acetic acid is 11.4 grams.

EXAMPLE 8B

Sodium [N,N-bis-(2-hydroxyethyl)aminoacetamido]-acetate.

[N,N-bis-(2-hydroxyethyl)aminoacetamido]acetic acid (4.405 grams, 0.02 mole) is suspended in water (10 ml) and sodium hydroxide (800 mg., 0.02 mole) in water (4 ml) is added with stirring. As soon as the solid has dissolved, water is added to bring the volume to 20 ml. The solution contains 25.9% by weight of, or is 1.11 molar in, sodium [N,N-bis-(2-hydroxyethyl)aminoacetamido]acetate.

EXAMPLE 8C

Sodium [N,N-bis-(2-hydroxyethyl)aminoacetamido]-acetate and sodium hydroxide.

By following the procedure described in Example 8b except that 936 mg. (0.02 moles) of sodium hydroxide is used instead of 800 mg. The final solution contains 25.9% by weight in sodium [N,N-bis-(2-hydroxymethyl)amino-acetamido]acetate, 0.68% by weight of, or is 0.17 molar in, sodium hydroxide, and contains 26.58% by weight in total solids.

EXAMPLE 9

Preparation of 2-[N,N-bis-(2-hydroxy-ethyl)amino-acetoxy]-2-methylpropanoic acid.

Bromoacetic acid (16.01 grams, 0.1 mole) is dissolved in tetra-hydrofuran (200 ml.) and 1,1-carbonyldiimidazole (16.22 grams, 0.1 mole) is added and the mixture stirred for an hour at 25° C. tert.-Butyl 2-hydroxy-2-methylpropanoate (10.41 grams, 0.1 mole) is added and the mixture stirred for 18 hours at 25° C. The solvent is removed by evaporation in vacuo to give tert. butyl 2-(2-bromoacetoxy)-2-methylpropanoate acid (0.1 mole). This compound is dissolved in ether, dried over anhydrous magnesium sulfate, filtered and the solvent removed by evaporation in vacuo. The product is dissolved in 1-propanol (100 ml.) and bis-(2-hydroxyethyl)amine (10.51 grams, 0.1 mole) and triethylamine (11.1 grams, 0.1 mole) are added and the mixture is stirred and heated at reflux for 3 hours. The volatile material is evaporated in vacuo, the residue dissolved in ether (250 ml.), washed with water and dried over anhydrous magnesium sulfate. The solvent is removed by evaporation in vacuo and dissolved in toluene (300 ml.). Methanesulfonic acid (2 grams) is added and the mixture refluxed for 2 hours. The mixture is cooled, extracted with water and the organic layer dried over anhydrous magnesium sulfate. The solvent is removed by evaporation in vacuo. The yield of 2-[N,N-bis-(2-hydroxyethyl)aminoacetoxy]-2-methylpropanoic acid is 17.45 g. (70%).

EXAMPLE 10

N-Methyl-N-[N,N-bis-(2-hydroxyethyl)aminoacetamido]-acetic acid and its sodium salt.

Step A: N,N-Bis-(2-acetoxyethyl)aminoacetic acid

N,N-Bis-(2-hydroxyethyl)aminoacetic acid (16.3 gm., 0.1 mole) is added to toluene (200 ml.) and acetic anhydride (22.46 gm., 0.22 mole) is added and the mixture stirred and heated at 100° C. for 3 hours. The volatile materials are removed by distillation in vacuo using a rotary evaporator. The residue is dissolved in ether (100 ml.) washed with water and dried over sodium carbonate and the solvent removed by evaporation in vacuo. The residue of N,N-bis-(2-acetoxyethyl)aminoacetic acid is used directly in the next step.

Step B: Methyl N-methyl-N-[N,N-bis-(2-acetoxyethyl) aminoacetamido]acetate

N,N-Bis-(2-acetoxyethyl)aminoacetic acid from Step A (24.73 gm., 0.1 mole) is dissolved in tetrahydrofuran (200 ml.) and 1,1'-carbonyldiimidazole (16.22 gm., 0.1 mole) added and the mixture stirred at 25° C. for an hour. Then, methyl sarcosinate (10.31 gm., 0.1 mole) is added and the mixture stirred at 25° C. for 16 hours. The solvent is removed by distillation in vacuo to give methyl N-methyl-N-[N,N-bis-acetoxyethyl)aminoacetamido]acetate which is used directly in the next step.

Step C: N-Methyl-N-[N,N-bis-(2-hydroxyethyl) aminoacetamido]acetic acid

Methyl N-methyl-N-bis-(2-acetoxyethyl) aminoacetamido]acetate (16.62 g., 0.05 mole) is dissolved in ethanol (150 ml.) and NaOH (680 mg., 0.17 mole) in water (75 ml.) and the mixture stirred and heated at 80° C. for 1 hour. The solution is cooled to room temperature and allowed to stand for 16 hours. The solution is acidified with 12 normal hydrochloric acid and the ethanol removed by evaporation in a rotary evaporator in vacuo. The residue is triturated with water and the solid removed by filtration, washed with water and dried. The product is purified by chromatography using a silica gel column on which the product is placed after dissolving in a little tetrahydro-furan and eluted with a mixture of methylene chloride/tetrahydro-furan/acetic acid 50/1/1 (by volume). There is obtained 9.2 g. of N-methyl-N-[N,N-bis-(2-hydroxyethyl) aminoacetamido]acetic acid.

Step D: Sodium N-methyl-N-[N,N-bis-(2-hydroxyethyl) acetamido]acetate

N-Methyl-N-(N,N-bis-(2-hydroxyethyl)acetamido]acetic acid (3.32 g., 0.01 mole) is suspended in water (5 ml.) and sodium hydroxide (400 mg., 0.01 mole) in water (2 ml.) is added. Water is added to bring the volume to 10.0 ml. The solution is 35.4% in solids or 1.0 molar in sodium N-methyl-[N,N-bis-(2-hydroxyethyl)aminoacetamido]-acetate.

EXAMPLE 11

Preparation of a solution of sodium 2-[N,N-bis-(2-hydroxyethyl)amino]-2-methylpropanoate plus sodium hydroxide for topical administration.

2-[N,N-bis-(2-hydroxyethyl)amino]-2-methylpropanoic acid (42.07 g., 0.22 mole) (Example 2a) is suspended in pyrogen-free distilled water (500 ml.) and treated with sodium hydroxide (10.3 g., 0.25 moles) in distilled pyrogen-free water (100 ml.). When the solid is dissolved, the solution is diluted to 1000 ml. with pyrogen-free distilled water. The solution is sterilized by filtration. The solution is 2.24% in total solids and 0.15% (0.04 molar) in NaOH. The resulting solution is used for applying to tissue surfaces by painting, using a sterile cotton swab, spraying from a bottle or from an atomizer.

In a similar way other molar ratios of sodium 2-[N,N-bis-(2-hydroxyethyl)amino]-2-methylpropanoate plus sodium hydroxide may be used, as well as other concentrations of total solids. Likewise, the other salts of 2-[N,N-bis-(2-hydroxyethyl)amino]-2-methylpropanoate listed in Example 4 using the other bases listed in Example 5 may be used instead of those listed above. In addition, the other hydroxyl ion modulating salts and bases listed in Examples 6, 7, 8, 9 and 10 may be substituted for the sodium 2-[N,N-bis-(2-hydroxyethyl)amino]-2-methylpropanoate and sodium hydroxide.

EXAMPLE 12

Preparation of a solution of sodium 2-[N,N-bis-(2-hydroxyethyl)amino]-2-methylpropanoate plus 2-[N,N-bis-(2-hydroxy-propyl)amino]-2-methyl-propanoate and sodium hydroxide for topical administration.

2-[N , N-bis-(2-hydroxyethyl)amino]-2-methylpropanoate (21.035 g., 0.11 mole) and 2-[N,N-bis-(2-hydroxypropyl)amino]-2-methylpropanoate (24.12 g., 0.11 mole) is suspended in pyrogen-free distilled water (500 ml.) and sodium hydroxide (10.3 g., 0.25 mole) in pyrogen-free distilled water (100 ml.). When all the solids had dissolved upon stirring, the solution is diluted to 1000 ml. using pyrogen-free distilled water.

The solution is sterilized by filtration. The solution contains 2.40% by weight of total solids and 0.15% by weight (0.038 molar) of NaOH. This solution is used for applying to tissue surfaces by painting, using a sterile cotton swab, spraying from a bottle or from an atomizer.

In a similar way other molar ratios of sodium 2-[N,N-bis-(2-hydroxyethyl)amino]-2-methylpropanoate plus sodium 2-[N,N-bis-(2-hydroxypropyl]amino-2-methylpropanoate to sodium hydroxide may be used, as well as other concentrations of total solids. Likewise, the other salts of 2-[N,N-bis-(2-hydroxyethyl)amino]-2-methylpropanoate listed in Example 4 and of 2-[N,N-bis-(2-hydroxypropyl]amino-2-methylpropanoate listed in Example 6 derived from the other bases listed in Examples 4 may be used instead of those listed above. In addition, mixtures of the other hydroxyl ion modulating salts and bases listed in Examples 3, 4, 5, 6, 7, 8, 9 and 10, may be used instead of sodium 2-[N,N-bis-(2-hydroxyethyl)amino] -2-methylpropanoate, sodium 2-[N,N-bis-(2-hydroxypropyl)amino-2-methylpropanoate and sodium hydroxide as described above.

EXAMPLE 13

Preparation of a solid mixture of sodium 2-[N,N-bis-(2-hydroxyethyl)amino]-2-methylpropanoate and sodium hydroxide.

One hundred ml. of the solution described in Example 11 consisting of sodium 2-[N,N-bis-(2-hydroxyethyl)amino]-2-methylpropanoate and 0.04 molar sodium hydroxide in pyrogen-free distilled water is lyophilized (freeze dried) to give a solid residue. This solid is used to regenerate a solution of any desired concentration by adding pyrogen-free distilled water. It also can be pulverized under sterile conditions and placed in a standard aerosol dispenser for administration to tissue surfaces by aerosol.

In a similar way other molar ratios of sodium 2-[N,N-bis-(2-hydroxyethyl)amino]-2-methylpropanoate to sodium hydroxide may be used, as well as other concentrations of total solids. Likewise, the other salts of 2-[N,N-bis-(2-hydroxyethyl)amino]-2-methylpropanoic acid listed in Example 4 and the other bases listed in Example 5 may be used instead of those listed above. In addition, the other hydroxyl ion modulating salts and bases listed in Examples 6, 7, 8, 9 and 10, may be substituted for the sodium 2-[N,N-bis-(2-hydroxyethyl)amino]-2-methylpropanoate and sodium hydroxide.

EXAMPLE 14

Preparation of ointments and creams containing sodium 2-[N,N-bis-(2-hydroxyethyl)amino]-2-methylpropanoate and sodium hydroxide.

The solid residue of sodium 2-[N,N-bis-(2-hydroxyethyl) amino]-2-methylpropanoate and sodium hydroxide obtained in Example 13 by lyophilization is pulverized under sterile conditions and mixed into standard ointments and creams so that the total concentration of sodium 2-[N,N-bis-(2-hydroxyethyl)amino]-2-methylpropanoate plus sodium hydroxide is in the range of 1% to 15% of the total mixture. These ointments and creams are applied to the tissues for wound healing therapy.

In a similar way other molar ratios of sodium 2-[N,N-bis-(2-hydroxyethyl)amino]-2-methylpropanoate and sodium hydroxide may be used, as well as other concentrations of total solids. Likewise, the other salts of 2-[N,N-bis-(2-hydroxyethyl)amino]-2-methylpropanoic acid listed in Example 4 and the other bases listed in Example 5 may be used instead of those listed above. In addition, the other hydroxyl ion modulating salts and bases listed in Examples 6, 7, 8, 9 and 10 may be substituted for the sodium 2-[N,N-bis(2-hydroxyethyl)amino]-2-methylpropanoate and sodium hydroxide.

While this invention has been described with respect to various specific examples and embodiments, it is to be understood that the invention is not limited thereto and that it can be variously practiced within the scope of the following claims.

What is claimed is:

1. A hydroxyl ion modulating compound having the following formula:

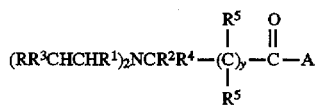

wherein each R is independently selected from the group consisting of H, alkyl, hydroxyalkyl, cycloalkyl, aryl and substituted counterparts thereof; each $R^1$ is independently selected from the group consisting of H, alkyl, hydroxyalkyl and substituted counterparts thereof; $R^2$ is selected from the group consisting of H, alkyl, cycloalkyl, aryl, aralkyl, heterocyclic, heterocyclicalkyl and substituted counterparts thereof; each $R^3$ is independently selected from the group consisting of H, alkyl, hydroxyalkyl, hydroxy, aryl, and substituted counterparts thereof; $R^4$ is selected from the group consisting of H, alkyl having 1 to 4 carbon atoms, lower alkenyl, lower alkynyl and phenyl; y is an integer in the range of zero to 3; each $R^5$ is independently selected from the group consisting of H and methyl; A is selected from the group consisting of $O^-Y^+$, $OCH_2COO^-Y^+$, $OCH(CH_3)COO^-Y^+$, $OC(CH_3)_2COO^-Y^+$, $NHCH_2COO^-Y^+$, $NHCH(CH_3)COO^-Y^+$, $NHC(CH_3)_2COO^-Y^+$, $N(CH_3)CH_2COO^-Y^+$ and $NH(CH_2)_2COO^-Y^+$; and $Y^+$ is selected from the group consisting of $H^{3O}$, $Na^+$, $K^+$, $Li^+$ $(CH_3)_4N^+$ and guanidinium, provided that in the event y is zero or A is $O^-Y^+$, then $R^2$ and $R^4$ are other than H, and at least one $(RR^3CHCHR^1-)$ includes a hydroxy group.

2. The hydroxyl ion modulating compound of claim 1 wherein each R is independently selected from the group consisting of H, alkyl having 1 to 4 carbon atoms, hydroxyalkyl having 1 to 4 carbon atoms, cycloalkyl, phenyl and substituted counterparts thereof; each $R^1$ is independently selected from the group consisting of H, alkyl having 1 to 3 carbon atoms, hydroxyalkyl having 1 to 3 carbon atoms and substituted counterparts thereof; $R^2$ is selected from the group consisting of H, alkyl having 1 to 5 carbon atoms, hydroxyalkyl having 1 to 5 carbon atoms, cycloalkyl having 3 to 6 carbon atoms, aryl, heterocyclic, heterocyclicalkyl and substituted counterparts thereof; each $R^3$ is independently selected from the group consisting of H, alkyl having 1 to 3 carbon atoms, hydroxyalkyl having 1 to 3 carbon atoms, hydroxy, aryl and substituted counterparts thereof; $R^4$ is selected from the group consisting of H, alkyl having 1 to 4 carbon atoms, lower alkenyl, lower alkyl and phenyl; and y is zero or

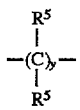

is selected from the group consisting of —CH$_2$—, —(CH$_2$)$_2$—, —(CH$_2$)$_3$—, —CH(CH$_3$)— and —C(CH$_3$)$_2$.

3. The hydroxyl ion modulating compound of claim 1 wherein each R is independently selected from the group consisting of H, CH$_3$, CH$_2$OH, and C$_6$H$_5$; each R$^1$ is independently selected from the group consisting of H, CH$_3$, CH$_2$OH and C$_2$H$_5$; R$^2$ is selected from the group consisting of H, CH$_3$, C$_2$H$_5$, CH$_3$CH$_2$CH$_2$—, HOCH$_2$—, cyclopropyl, phenyl, pyridyl, imidazolyl and pyrimidyl; each R$^3$ is independently selected from the group consisting of H, OH, CH$_3$ and C$_2$H$_5$; R$^4$ is selected from the group consisting of H, vinyl, ethynyl, alkyl having 1 to 4 carbon atoms and phenyl; and y is zero or

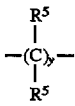

is selected from the group consisting of —CH$_2$—, —(CH$_2$)$_2$—, —(CH$_2$)$_3$—, —CH(CH$_3$)— and —C(CH$_3$)$_2$—.

4. The hydroxyl ion modulating compound of claim 1 selected from the group consisting of sodium salts of an acid, potassium salts of an acid, tetramethylammonium salts of an acid and guanidinium salt of an acid; said acid being selected from the group consisting of 2-[N,N-bis-(2-hydroxyethyl)amino]-2-methylpropanoic acid, 2-[N,N-bis-(2-hydroxypropyl)amino]-2-methylpropanoic acid, 2-[N-(2-hydroxyethyl)-N-(2-hydroxypropyl)amino]-2-methylpropanoic acid, 2-[N,N-bis-(2-hydroxyethyl)amino]-2-methylbutanoic acid, the racemate, the D-enantiomer and the L-enantiomer, 2-[N,N-bis-(2-hydroxyethyl)amino]-2-phenylpropanoic acid, 2-[N,N-bis-(2-hydroxyethyl)aminoacetoxy]-2-methylpropanoic acid,

[N,N-bis-(2-hydroxyethyl)aminoacetamido]acetic acid,

N-methyl-N-(N,N-bis-(2-hydroxyethyl)aminoacetamido] acetic acid,

3-[N,N-bis-(2-hydroxyethyl)amino]propanoic acid,

4-[N,N-bis-(2-hydroxyethyl)amino]butanoic acid, the racemate, the D-enantiomer and the L-enantiomer, 2,2-dimethyl-3-[N,N-bis-(2-hydroxyethyl)amino]propanoic acid, 2-[N,N-bis-(9-hydroxyethyl)amino]-2-(3-pyridyl)propanoic acid, 2-[N,N-bis-(2,3-dihydroxypropyl)amino]-2-methylpropanoic acid, 2-[N,N-bis-(1-hydroxy-2-propyl)amino]-2-methylpropanoic acid, 2-[N,N-bis-(2-hydroxy-2-phenylethyl)amino]-2-methylpropanoic acid, 2-[N,N-bis-(1,3-dihydroxy-2-propyl)amino]-2-methylpropanoic acid, and 2-[N,N-bis-(3-hydroxypropyl)amino]-2-methylpropanoic acid.

5. A pharmaceutical composition useful in providing a desired therapeutic effect when administered to a human or an animal, said desired therapeutic effect being selected from the group consisting of ocular therapeutic effects, oral therapeutic effects, ear, nose and throat therapeutic effects, dermal therapeutic effects, topical therapeutic effects, dental therapeutic effects, analgesic therapeutic effects, wound therapeutic effects and internal therapeutic effects, said pharmaceutical composition comprising:

a therapeutically effective amount of a hydroxyl ion component and an effective amount of a hydroxyl ion modulating component, said hydroxyl ion modulating component being selected from the group consisting of compounds having the following formula

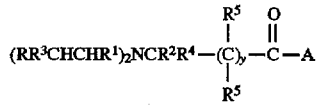

derivatives thereof and mixtures thereof, wherein each R is independently selected from the group consisting of H, alkyl, hydroxyalkyl, cycloalkyl, aryl and substituted counterparts thereof; each R$^1$ is independently selected from the group consisting of H, alkyl, hydroxyalkyl and substituted counterparts thereof; R$^2$ is selected from the group consisting of H, alkyl, cycloalkyl, aryl, aralkyl, heterocyclic, heterocyclicalkyl and substituted counterparts thereof; each R$^3$ is independently selected from the group consisting of H, alkyl, hydroxyalkyl, hydroxy, aryl and substituted counterparts thereof; R$^4$ is selected from the group consisting of H, alkyl having 1 to 4 carbon atoms, lower alkenyl, lower alkynyl and phenyl; y is an integer in the range of zero to 3; each R$^5$ is independently selected from the group consisting of H and methyl; each A is selected from the group consisting of O$^-$Y$^+$, OCH$_2$COO$^-$Y$^+$, OCH(CH$_3$)COO$^-$Y$^+$, OC(CH$_3$)$_2$COO$^-$Y$^+$, NHCH$_2$COO$^-$Y$^+$, NHCH(CH$_3$)COO$^-$Y$^+$, NHC(CH$_3$)$_2$COO$^-$Y$^+$, N(CH$_3$)CH$_2$COO$^-$Y$^+$ and NH(CH$_2$)$_2$COO$^-$Y$^+$; and Y$^+$ is selected from the group consisting of H$^+$, Na$^+$, K$^+$, Li$^+$, (CH$_3$)$_4$N$^+$ and guanidinium, and mixtures thereof, provided that in the event y is zero or A is O$^-$Y$^+$, then R$^2$ and R$^4$ are other than H.

6. The pharmaceutical composition of claim 5 wherein each R is independently selected from the group consisting of H, alkyl having 1 to 4 carbon atoms, hydroxyalkyl having 1 to 4 carbon atoms, cycloalkyl, phenyl and substituted counterparts thereof; each R$^1$ is independently selected from the group consisting of H, alkyl having 1 to 3 carbon atoms, hydroxyalkyl having 1 to 3 carbon atoms and substituted counterparts thereof; R$^2$ is selected from the group consisting of H, alkyl having 1 to 5 carbon atoms, hydroxyalkyl having 1 to 5 carbon atoms, cycloalkyl having 3 to 6 carbon atoms, aryl, heterocyclic, heterocyclicalkyl and substituted counterparts thereof; each R$^3$ is independently selected from the group consisting of H, alkyl having 1 to 3 carbon atoms, hydroxyalkyl having 1 to 3 carbon atoms, hydroxy, aryl and substituted counterparts thereof; R$^4$ is selected from the group consisting of H, alkyl having 1 to 4 carbon atoms, lower alkenyl, lower alkynyl and phenyl; and y is zero or

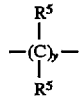

is selected from the group consisting of —CH$_2$—, —(CH$_2$)$_2$—, —(CH$_2$)$_3$—, —CH(CH$_3$)— and —C(CH$_3$)$_2$—.

7. The pharmaceutical composition of claim 5 which is ophthalmically acceptable and is useful as an agent in providing ocular therapeutic effects.

8. The pharmaceutical composition of claim 5 which is useful as an agent in providing dental therapeutic effects.

9. The pharmaceutical composition of claim 5 wherein said hydroxyl ion modulating component is present in a molar concentration greater than the molar concentration of hydroxyl ion.

10. The pharmaceutical composition of claim 9 which has a molar ratio of hydroxyl ion modulating component to hydroxyl ion in the range of about 2.5 to about 12.

11. The pharmaceutical composition of claim 9 which is useful as an agent for wound healing.

12. A method for providing a desired therapeutic effect to a human or an animal which comprises:

administering to said human or said animal an amount of the pharmaceutical composition of claim 5 effective to provide said desired therapeutic effect to said human or said animal, said desired therapeutic effect being selected from the group consisting of ocular therapeutic effects, oral therapeutic effects, ear, nose and throat therapeutic effects, dermal therapeutic effects, topical therapeutic effects, dental therapeutic effects, analgesic therapeutic effects, wound therapeutic effects and internal therapeutic effects.

13. A method for providing a desired therapeutic effect to a human or an animal which comprises:

administering to said human or said animal an amount of the pharmaceutical composition of said claim 6 effective to provide said desired therapeutic effect to said human or said animal, said desired therapeutic effect being selected from the group consisting of ocular therapeutic effects, oral therapeutic effects, ear, nose and throat therapeutic effects, dermal therapeutic effects, topical therapeutic effects, dental therapeutic effects, analgesic therapeutic effects, wound therapeutic effects and internal therapeutic effects.

14. A method for providing a desired therapeutic effect to a human or an animal which comprises:

administering to said human or said animal an amount of the pharmaceutical composition of claim 7 effective to provide said desired therapeutic effect to said human or said animal, said desired therapeutic effect being selected from the group consisting of ocular therapeutic effects, oral therapeutic effects, ear, nose and throat therapeutic effects, dermal therapeutic effects, topical therapeutic effects, dental therapeutic effects, analgesic therapeutic effects, wound therapeutic effects and internal therapeutic effects.

15. A method for providing a desired therapeutic effect to a mammalian eye which comprises:

administering to said mammalian eye an amount of the pharmaceutical composition of claim 7 effective to provide said desired therapeutic effect to said mammalian eye.

16. A method for effecting analgesia to a human or an animal which comprises:

administering to the eye of said human or animal an effective amount of the pharmaceutical composition of claim 7 at conditions effective to impart an analgesic benefit to said human or animal.

17. A method for providing a desired therapeutic effect to a human or an animal which comprises:

administering to said human or said animal an amount of the pharmaceutical composition of claim 5 effective to provide said desired therapeutic effect to said human or said animal, said desired therapeutic effect being the management of at least one disease selected from the group consisting of gingivitis and gingivitis-related dental diseases.

18. A method for providing a desired therapeutic effect to a human or an animal which comprises:

administering to said human or said animal an amount of the pharmaceutical composition of claim 5 effective to provide said desired therapeutic effect to said human or said animal, said desired therapeutic effect is the management of at least one skin lesion.

* * * * *